(12) United States Patent
Fjerdingstad et al.

(10) Patent No.: US 7,921,739 B2
(45) Date of Patent: Apr. 12, 2011

(54) IN SITU SAMPLING AND MONITORING A FLUID

(76) Inventors: Sølve J. Fjerdingstad, Oslo (NO); John F. Reintjes, Alexandria, VA (US); John E. Tucker, Centreville, VA (US); Lawrence L. Tankersley, Annapolis, MD (US)

( * ) Notice: Subject to any disclaimer, the term of this patent is extended or adjusted under 35 U.S.C. 154(b) by 69 days.

(21) Appl. No.: 12/153,716

(22) Filed: May 22, 2008

(65) Prior Publication Data

US 2009/0007700 A1    Jan. 8, 2009

Related U.S. Application Data

(63) Continuation of application No. 10/540,114, filed as application No. PCT/NO03/00431 on Dec. 19, 2003, now abandoned.

(30) Foreign Application Priority Data

Dec. 20, 2002   (NO) .................................. 20026178

(51) Int. Cl.
*G01N 1/20* (2006.01)
*G01N 15/02* (2006.01)
(52) U.S. Cl. ................... 73/863.71; 73/61.43; 73/61.44; 73/61.48; 73/61.59; 73/64.56
(58) Field of Classification Search .................. 73/61.41, 73/61.43, 61.44, 61.48, 61.59, 64.56, 863.71
See application file for complete search history.

(56) References Cited

U.S. PATENT DOCUMENTS 4,905,510 A    3/1990   Brickhouse
(Continued)

FOREIGN PATENT DOCUMENTS
GB    2 090 814 A    7/1982
(Continued)

OTHER PUBLICATIONS

Press Release dated Feb. 29, 2000, Spectro, Inc., "Lockheed Martin and Spectro Join Forces to market Lasernet Fines Machinery Wear Analysis Breakthrough".

(Continued)

*Primary Examiner* — Daniel S Larkin

(74) *Attorney, Agent, or Firm* — Finnegan, Henderson, Farabow, Garrett & Dunner, L.L.P.

(57) ABSTRACT

A method for in situ sampling and monitoring of a fluid flowing in a flow path, whereby the fluid is to be directed to a chamber a first valve may provide a connection between an inlet to the chamber and the flow path and a second valve may provide a connection between an outlet from the chamber and the flow path, comprising the following steps: a) opening the first valve and the second valve to let the incoming fluid flow through the inlet to the chamber and from the chamber through the outlet into the continuation of the fluid path, thereby allowing fluid to circulate through the chamber for a certain time, b) trapping the fluid in the chamber by closing the second valve and thereafter closing the first valve, c) opening a valve 9 for reducing pressure, to obtain a pressure in the chamber suitable for monitoring the fluid, d) opening an access valve 11 and leading the fluid trapped in the chamber into a monitor system wherein the fluid is analyzed, and thereby providing the data representing the fluid characteristics, e) providing exit for the fluid analyzed through a further fluid path possibly to a low pressure section of the system.

13 Claims, 3 Drawing Sheets

U.S. PATENT DOCUMENTS

| | | | |
|---|---|---|---|
| 5,370,005 | A | 12/1994 | Fjerdingstad |
| 5,572,320 | A | 11/1996 | Reintjes et al. |
| 5,619,333 | A | 4/1997 | Staff et al. |
| 6,049,381 | A | 4/2000 | Reintjes et al. |
| 6,104,483 | A | 8/2000 | Sebok et al. |
| 6,182,505 | B1 | 2/2001 | Segeral |
| 6,270,059 | B1 | 8/2001 | Kurzer et al. |
| 6,612,156 | B1 | 9/2003 | Hakimuddin |
| 2003/0030810 | A1 | 2/2003 | Sebok et al. |
| 2003/0164944 | A1 | 9/2003 | Nieuwenhuis et al. |
| 2003/0209647 | A1 | 11/2003 | Miller et al. |
| 2004/0165185 | A1 | 8/2004 | Reintjes et al. |

FOREIGN PATENT DOCUMENTS

| | | |
|---|---|---|
| WO | WO 99/00656 | 1/1999 |

OTHER PUBLICATIONS

Press Release dated Mar. 17, 2003, Lockheed Martin, "http://www://lockheedmartin.com/news/articles/022003_2.html".

Press Release dated Feb. 25, 2003, Lockheed Martinand FRAS Develop Autonomus Lasernet Fines for hands-Off Lubricant Sampling, "http://ness/external.lmco.com/news/03feb20akron.html".

Press Release dated Apr. 1, 2002, "Navy' new Gunk-O-Lyzer?", Office of Naval Research, http://www.onr.navy.mil/media/tipoff_display.asp?ID=26.

"Lasernet Optical Oil Sensor", Sep. 2002, Naval Research Laboratory, "http://techtransfernrl.navy.mil/pdfs/s07-oildebris.pdf".

Reintjes et al., "Application of LaserNet Fines to Mechanical Wear and hydraulic Monitoring", DSTO International Conference on Health and Usage Monitoring, Melbourne, Feb. 19-20, 2001, SDTO-GD-0262.

IN SITU SAMPLING AND MONITORING A FLUID

This application is a continuation of U.S. application Ser. No. 10/540,114, filed May 12, 2006, now abandoned, which is a §371 of International Application No. PCT/NO2003/000431 filed Dec. 19, 2003, which claims priority of Norwegian Application No. 20026178, filed Dec. 20, 2002, the contents of all of which are incorporated herein by reference.

BACKGROUND OF THE INVENTION

The present invention relates to a method for in situ sampling and monitoring of a fluid flowing in a flow path. Furthermore the invention relates to an apparatus for in situ sampling and monitoring of a fluid flowing in a flow path.

The present invention may be utilized for sampling and analyzing/monitoring the condition of any kind of fluid, but may be especially suitable for analysis of particulates in a flowing fluid. The term monitoring will be used in the following, this term is meant also to include analyzing.

Analysis of debris particles in lubricating oil is a well-known method of monitoring the condition of oil wetted machinery. Particulate monitoring is also an important maintenance procedure for hydraulic systems. One commonly used method for performing the analysis is to withdraw a sample of fluid from the equipment manually and physically transport it to a laboratory for analysis. Once at the laboratory, various tests are performed, including particle counting and microscopic analysis of debris particles. Various methods are used for sample preparation for microscope analysis, including centrifugal separation, filterpatch and ferroaraphy. Once prepared, the samples are examined by a human expert and machine condition at the time the sample was taken is identified by subjective evaluation of the sample.

While this procedure is effective in some circumstances, it has deficiencies that reduce its effectiveness and raise its cost in many applications. Among the deficiencies are the long delay from drawing of the sample to receipt of analysis report, the need for sample preparation, the subjective evaluation of samples and the inherent inaccuracy of sampling as it is currently done from drain ports or sumps. In addition, the mere need for drawing a sample manually contributes to the maintenance workload and expense. In addition, it can often miss transient debris production that can be indicative of certain mechanical malfunctions.

Some of these deficiencies are addressed in known technologies. The inaccuracy of sampling is addressed with the on line fluid sampler in NO 171430 in which particles from the fall flow are captured in a sample bottle for transport and analysis.

Sample preparation and subjective evaluation are addressed in LaserNet Fines (LNF) by NRL and in U.S. Pat. No. 5,572,320 in which particles from a sample bottle are analyzed and classified automatically with computer classifiers, and quantitative measures of debris characteristics based on size and shape distributions are produced for evaluation of machine condition. LaserNet Fines also address the deficiency of long delay times between sample draw and report by being installed on site (or on ship or platform, depending on the circumstances).

LaserNetFines is a technology for identification of mechanical wear in oil-wetted machinery, but could also be used to survey the conditions of other kinds of fluid: LaserNetFines determines fault type and severity by measurement of size distribution, concentration, rate of production and shape characteristics of wear particles. It also detects and measures free water and fiber content and is applicable for cleanliness determination in hydraulic systems. The LaserNet Fines technology is compatible with implementation as a benchtop bottle sample analyzer or with on line operation for particle analysis without drawing a sample. To data LaserNet Fines has been implemented for mechanical wear and hydraulic monitoring as a bottle sampler.

Accurate sampling of the particulate content of the circulating fluid is vital to effective mechanical-wear or hydraulic-contamination monitoring. Inaccuracies associated with sampling through drain ports or other diverted flow—paths can easily lead to erratic trending results. In NO 171430 a full flow on-line sampler is introduced to provide accurate bottle sampling of the particles in the full flow of an oil system.

Neither of these technologies alone address the deficiency of the requirement of manually drawn samples with their accompanying expense and demand on workload. However, these publications provide the basis for the current invention; the complete document of NO 171430, the complete document of U.S. Pat. No. 5,572,320 and publication on LNF "On Line Operation of LaserNet Fines With Accurate Sampling", Reintjes et al, should therefore be considered included as a whole in this current patent application.

The present invention combines in one embodiment a monitor system such as the LaserNet Fines with the fluid sampler in NO 171430 for accurate particle monitoring or any other monitoring of the fluid. LaserNet Fines can be operated on line on a laboratory flow loop. Particle counting and imaging results can be utilized for a variety of flow conditions. On line results are compared to bottle sample results for the same conditions.

The new aspects of this invention are the method and apparatus of obtaining simultaneously automatic on line reliable sampling of debris particles in fluid systems and automatic quantitative assessment of equipment condition through analysis of size and shape characteristics of the particles. Prior art outside of the two technologies included here suffer from inaccuracies in manually drawn samples originating in non-repeatable aspects of sampling, and from non-quantitative assessment of debris particles. Existing on line debris monitors that count and size particles cannot identify the type of mechanical fault responsible for the wear, and therefore cannot address the severity of the problem. The combination of the fluid sampler in NO 171430 and the LaserNet Fines debris monitor that the full power of on line sampling and debris analysis is realized. The invention covers method and apparatus for obtaining debris analysis based on size and shape characteristics with automatic on line operation and transmission of the analysis data to a remote site.

One object of this invention is to address the deficiency of the long delay and expense due to manual sample extraction and transport with method and apparatus by combining the sampling procedure in NO 171 430 with a monitor system such as the LNF in a manner that allows on line-automatic monitoring, eliminating the need for manual sampling and sample preparation for analysis.

It is a second object of this invention to provide for transmission of the analysis carried out in the monitor system, to a remote site, eliminating the need for travel to the equipment for data retrieval.

SUMMARY OF THE INVENTION

These objects are attained according to the invention by a method for in situ sampling and monitoring/analyzing a fluid flowing in a flow path where the fluid is to be directed to a chamber. A first valve may be provided to obtain a connection between an inlet to the chamber and the flow path. A second valve may be provided to obtain a connection between an outlet from the chamber and the flow path.

The method comprises the following steps:
a) opening the first valve and the second valve to let the incoming fluid flow through the inlet to the chamber and from the chamber through the outlet into the continuation of the fluid path, thereby allowing fluid to circulate through the chamber for a certain time;
b) trapping the fluid in the chamber by closing the second valve and thereafter closing the first valve;
c) opening a valve for reducing pressure, to obtain a pressure in the chamber suitable for monitoring the fluid;
d) opening an access valve and leading the fluid trapped in the chamber into a monitor system wherein the fluid is analyzed, and thereby providing data representing the fluid characteristics; and
e) providing an exit for the fluid analyzed through a further fluid path possibly to a low pressure section of the system.

In one embodiment of the method according to the invention the valve for reducing pressure is to be opened for the chamber to communicate with an expansion chamber or some other structure which is capable of containing fluid. A valve for relieving pressure is opened to allow air to enter the chamber to maintain the pressure in the chamber, as the fluid is withdrawn from the chamber. Furthermore the fluid may be led into the monitor system by the effect of an internal pump of the monitor system.

The monitor system according to the invention may comprise a various range of system accommodated to the fluid which is to be monitored. In one embodiment the monitor system for analyzing the fluid and the possible particles therein, may be an optical system comprising a light source, an optical detector, means for processing data in accordance with the system described in U.S. Pat. No. 5,572,320. In another embodiment of the invention the monitor system is applicable for fluid containing particles such as an oil system, in which the monitor system can be adapted to monitor mechanical wear or hydraulic contamination in the fluid. The monitor system may then comprise a system wherein the particles in the fluid are analyzed and classified automatically with computer classifiers. Furthermore this monitor system includes quantitative measurements of debris characteristics based on size and shape distributions produced for evaluation of machine condition, concentration, measures of free water and fiber content. The system in applicable for cleanliness determination in a hydraulic system.

The data from the fluid analyzed in the monitor system can be stored locally, and/or transferred to a remote computer for evaluation or maintenance support, wherein the data can be transferred automatically after each analysis record, after an accumulation of a number of analyses record, or on a time sequence or on demand by a local or remote operator.

The invention also concerns an apparatus for in situ sampling and monitoring a fluid flowing in a flow path comprising:
an inlet and an outlet connected to a chamber;
a first valve provided for connecting an inlet to the flow path;
a second valve provided for connecting an outlet to the flow path; thereby allowing the fluid to fill the chamber, circulate the fluid through the chamber for a certain time, and capturing the fluid in the chamber;
an access valve provided for leading the fluid which is captured in the chamber into a monitor system where the fluid is to be analyzed; and
a valve for reducing pressure is provided to obtain a pressure in the chamber suitable for the monitor system.

Furthermore the apparatus may comprise a valve for relieving pressure provided for allowing air to enter the chamber to maintain the pressure in the chamber as the fluid is withdrawn from the chamber.

The apparatus may also comprise an expansion chamber communicating with the chamber through the pressure reducing valve, which expansion chamber provides the conditions for reducing the pressure in the chamber.

BRIEF DESCRIPTION OF THE DRAWINGS

Embodiments of the invention will now be described, by way of example only, by reference to the accompanying drawings, in which.

DETAILED DESCRIPTION OF THE INVENTION

Figure 1:
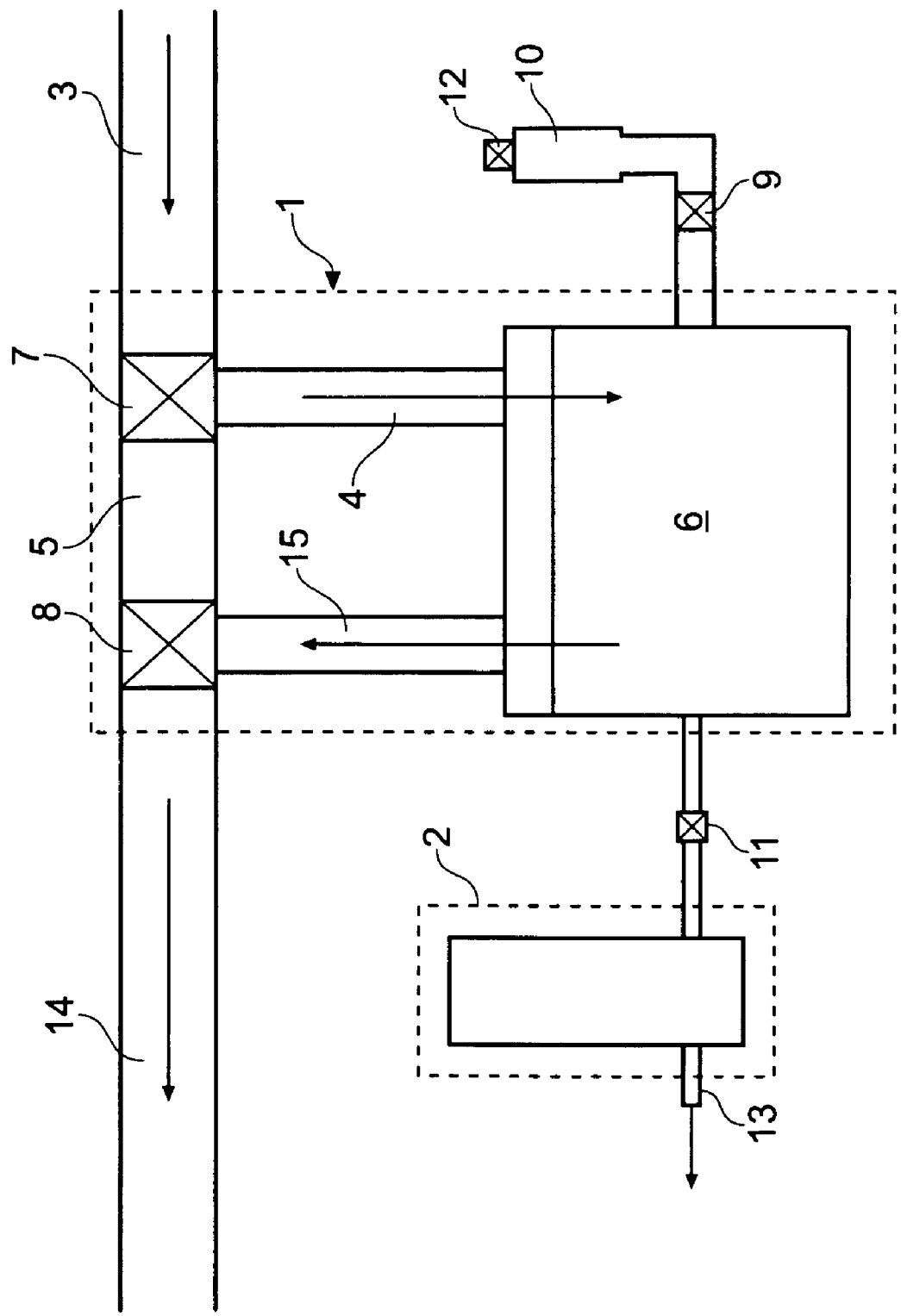
FIG. 1 shows a view of the general arrangement of the invention.

The apparatus illustrated in FIG. 1 comprises a fluid sampler 1 and monitor system 2, such as a LNF debris monitor system, with modifications to allow automatic on line operation. The fluid sampler 1 is connected into the fluid flow comprising a first flow path 3, a second flow path 5 and a third flow path 14 as shown in FIG. 1. It should be mentioned that the fluid sampler can be connected to the fluid flow line in a parallel type connection or in series type connection. With the fluid sampler is the provision for directing incoming fluid in the first flow path 3 through a flow section comprising a first flow section 4 (inlet) and a second flow section 15 (outlet) connected to a capture chamber 6, or through the second flow path 5. The choice being made by the position of first and second valves 7 and 8.

When the first and second valves 7 and 8 are in position for normal flow, the full flow with a full complement of debris particles flows through flow path 5. When the valves 7 and 8 are in position for diverted flow the full flow passes through first and second flow sections 4, 15. The fluid trapped in chamber 6 is now static and available for analysis. Valve 9 is then opened to reduce pressure in chamber 6 to a level suitable for the monitor system 2. An expansion chamber 10 can be provided in this purpose. An access valve 11 is then opened to allow access to the fluid in the chamber 6 by the monitor system 2. Fluid is drawn through the monitor system 2 by its internal pump and the fluid and/or its debris is analyzed.

Valve 12 is a pressure relief valve that opens to allow air to enter chamber 6 as the fluid is withdrawn from chamber 6 through the monitor system 2 in order to maintain the pressure in chamber 6 at about one atmosphere.

Fluid that has passed through the monitor system 2 is returned through flow path 13 to a low pressure section of the oil system. Fluid that flows through either the second flow path 5 or the first and second sections 4, 15 and chamber 6 is directed to the remainder of the equipment in the third flow path 14.

Valves 7, 8, 9 and 11 are preferably implemented as electrically controlled and operated valves. Their operation sequence is controlled by suitable programming to allow automatic operation, and can be implemented to operate either in a predetermined timing pattern or on demand by a local or remote operator. The data from the monitor system, such as a LNF analysis can be stored locally on suitable information media. In addition it can be transferred, for instance by electronic, optical means or by a modem, to a remote site for evaluation or maintenance support as determined by suitable computer commands. Transfer of data can be automatically done after each analysis record, after an accumulation of a number of analysis records, on a timed sequence or on demand by a local or remote operator.

Figure 2:
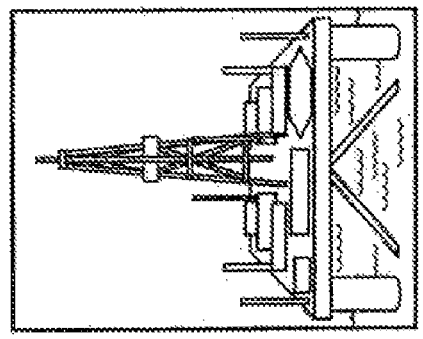
FIG. 2 shows a view of a system for transferring data from the test station to a remote site.
Figure 2:
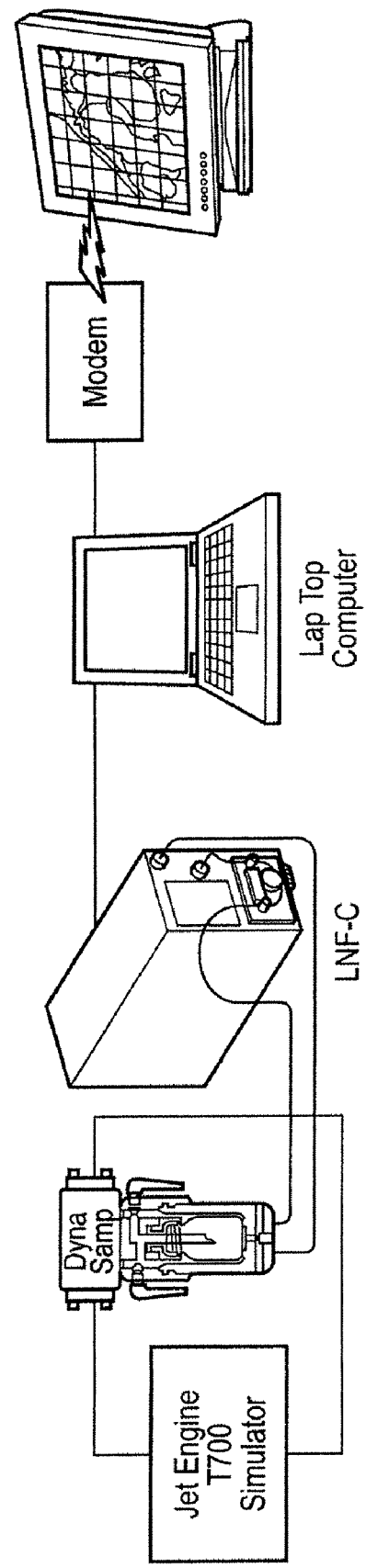

FIG. 2 illustrates the fluid sampler, named "Dynasamp" and a monitor system, named "LNF-C" in a system where data is transferred from the monitor system to a computer and via a modem to a remote site.

Figure 3:
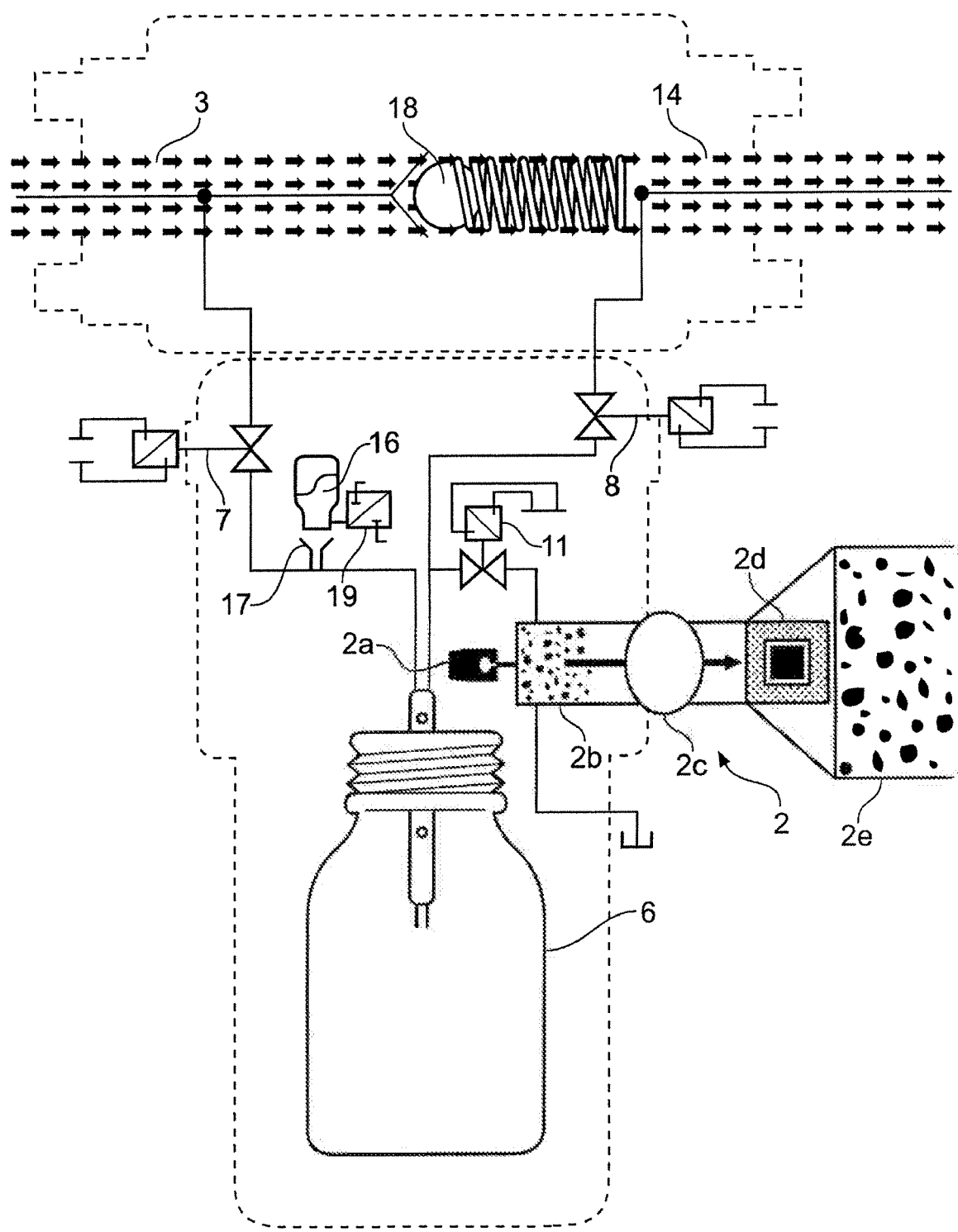
FIG. 3 shows a view of one embodiment of the invention.

FIG. 3 illustrates an embodiment of the invention as shown in FIG. 1. A flow regulator 18 has been provided in the fluid flow line, and the valves 7, 8, 11 are automatic valves which may be electrically controlled. The chamber 6 comprises a sampling bottle, preferably made of glass. The monitor system 2 is constituted by a laser diode 2a, a lens 2c which may have a magnitude of 4× and a camera 2d (for instance CCD/CMOS camera, 2 Mpix). The wear debris are illustrated by 2b and the TV rate camera image processing shape classification by 2e. Within the scope of the invention other monitor systems may be utilized, for instance an infrared light for examining the properties of the fluid; such as water content and viscosity. Also a gas chromatograph for carrying out the analysis in the sample bottle may be used.

In the embodiment shown in FIG. 3 the expansion chamber shown in FIG. 1 is left out. The system in FIG. 3 is provided with a gas cavity 16, which function is to be described in the following:

When a hydraulic system is operating under high pressure, it is possible to use the pressure, already generated in the system to feed the monitoring system 2 with the oil from the sampling bottle 6. The gas cavity 16 is used to give an accumulator effect for the pressure needed to feed the monitor system 2 with oil.

During operation with the valves 7, 8 in a fully open position, the pressure in the chamber 6 is working at system pressure. The gas cavity 16, which contains a separation membrane between the liquid fluid and gas, is loaded via an internal check valve 17, allowing the pressure to build up in the gas cavity 16.

The valves 7, 8 are then closed to capture a representative sample in the chamber 6, and the pressure is unloaded via the electrically operating access valve 11, which isolates the monitor system 2 from the chamber 6 in the fluid sampling device.

As the oil is practically incompressible, the pressure in the chamber 6 will very quickly drop to atmospheric pressure. By utilising a solenoid 19 to operate the check valve 17, which is keeping the gas cavity 16 still loaded with system pressure, the gas will pressurise the inlet of the sampling bottle and force the fluid through the monitor system through the access valve 11 which is still in an open position. In this case no internal pump is needed in the monitor system 2. Particle analyses from the oil can now be analysed by the image analysis system of the monitor system 2, (such as the LaserNet monitor).

Many alternative embodiments can be identified that fall within the purview of this disclosure. The expansion chamber can take the form of a short section of pipe or tubing. Alternatively it can be done away with altogether, and the high pressure can be reduced by expansion of flexible tubing between the fluid sampler and the monitor system. It will be obvious to the skilled person that the reduction of the pressure in the chamber 6 may be obtained in various ways within the scope of the invention. Conditions for normal and diverted flow can be reversed. Remote data transfer can be implemented or data can remain on board, if the test station is on board a vessel.

The invention claimed is:

1. A method for in situ sampling and monitoring of a fluid flowing in a flow path, where the fluid is to be directed to a chamber,
   where a first flow section and a second flow section provide connections for fluid flow between the chamber and the flow path and where a first valve is provided to allow the fluid to flow through the first flow section and,
   a second valve is provided to allow the fluid to flow through the second flow section, the method comprising the following steps:
   a) opening the first valve and the second valve to let the fluid flow through the first flow section to the chamber and from the chamber through the second flow section into a continuation of the fluid flow path;
   b) allowing fluid to circulate through the chamber for a certain time and loading a gas cavity which comprises a separation membrane separating the gas in the gas cavity and the fluid being loaded, thereby allowing pressure to build up in the gas cavity;
   c) trapping the fluid in the chamber by closing the second valve and thereafter closing the first valve;
   d) opening a valve for reducing the pressure, to obtain a pressure in the chamber which is suitable for monitoring the fluid;
   e) using the accumulated pressure in the gas cavity to force the fluid trapped in the chamber into a monitor system through an access valve wherein the fluid is analyzed, and thereby providing data representing characteristics of the fluid; and
   f) providing an exit for the fluid analyzed through a further fluid path.

2. The method according to claim 1,
   further comprising analyzing the fluid and possible particles therein by the monitor system which is an optical system comprising a light source, an optical detector and means for processing data.

3. The method according to claim 1,
   further comprising storing the data from the analyzed fluid, and/or transferring the data to a remote computer for evaluation or maintenance support, wherein the data can be transferred automatically after each analysis record, after an accumulation of a number of analyses record, or on a time sequence or on demand by a local or remote operator.

4. An apparatus for in situ sampling and monitoring of a fluid flowing in a flow path, the apparatus comprising:
   a first flow section connecting the flow path and a chamber and a second flow path connecting the flow path and the chamber;
   a first valve allowing the fluid to flow through the first flow section and a second valve allowing the fluid to flow through the second flow section such that the fluid can fill the chamber, to circulate through the chamber for a certain time and to be captured in the chamber;
   an access valve for reducing pressure in the chamber to a level suitable for a monitor system and allowing the fluid to flow from the chamber to the monitor system where the fluid is to be analyzed; and
   a gas cavity which is provided with a separation membrane separating gas in the gas cavity and fluid being loaded in the gas cavity during circulation of the fluid through the chamber such that the pressure which has been built up in the gas cavity, can be used to force the fluid in the chamber through the monitor system.

5. The apparatus according to claim 4, wherein the gas cavity is provided with a check valve, which is operated by a solenoid.

6. The apparatus according to claim 4 or 5, wherein the monitor system is an optical system comprising a light source, an optical detector, and means for processing data.

7. The apparatus according to claim 4 or 5, wherein the monitor system is connected to a computer, for transferring the data of the analyzed fluid, possibly to a remote site for evaluation or maintenance support, wherein the data can be transferred automatically after each analysis record, after an accumulation of a number of analyses record, or on a time sequence or on demand by a local or remote operator.

8. A method for in situ sampling and monitoring of a fluid flowing in a flow path, where the fluid is to be directed to a chamber, where a first flow section and a second flow section provide connections for fluid flow between the chamber and the flow path, and where a first valve is provided to allow the fluid to flow through the first flow section and a second valve is provided to allow the fluid to flow through the second flow section, the method comprising the following steps:
   a) opening the first valve and the second valve to let the fluid flow through the first flow section to the chamber and from the chamber through the second flow section into a continuation of the fluid flow path;
   b) allowing fluid to circulate through the chamber for a certain time;
   c) trapping the fluid in the chamber by closing the second valve and thereafter closing the first valve;
   d) opening a valve such that the chamber communicates with an expansion chamber for reducing the pressure to obtain a pressure in the chamber which is suitable for monitoring the fluid;
   e) opening an access valve and feeding the fluid trapped in the chamber into a monitor system through the access valve wherein the fluid is analyzed, and thereby providing data representing characteristics of the fluid; and
   f) providing an exit for the fluid analyzed through a further fluid path.

9. The method according to claim 8, further comprising opening a valve for maintaining pressure in the chamber.

10. The method according to claim 8 or 9, further comprising leading the fluid into a monitor system by the effect of an internal pump of the monitor system.

11. An apparatus for in situ sampling and monitoring a fluid flowing in a flow path, the apparatus comprising:
   a first flow section connecting the flow path and a chamber and a second flow section connecting the flow path and the chamber;
   a first valve allowing the fluid to flow through the first flow section and a second valve allowing the fluid to flow through the second flow section such that the fluid can fill the chamber, to circulate through the chamber for a certain time and to be captured in the chamber;
   an access valve which allows the fluid to flow from the chamber into a monitor system where the fluid is to be analyzed; and
   an expansion chamber communicating with the chamber through a valve such that the pressure in the chamber can be reduced to a level suitable for the monitor system.

12. The apparatus according to claim 11, further comprising a valve for relieving pressure, the valve allowing air to enter the chamber as the fluid is withdrawn from the chamber through the monitor system.

13. The apparatus according to claim 11 or 12, wherein the monitor system is connected to a computer, for transferring the data of the analyzed fluid, possibly to a remote site for evaluation or maintenance support, wherein the data can be transferred automatically after each analysis record, after an accumulation of a number of analyses record, or on a time sequence or on demand by a local or remote operator.

* * * * *